(12) United States Patent
Park et al.

(10) Patent No.: US 8,399,830 B2
(45) Date of Patent: Mar. 19, 2013

(54) MEANS AND METHOD FOR FIELD ASYMMETRIC ION MOBILITY SPECTROMETRY COMBINED WITH MASS SPECTROMETRY

(75) Inventors: Melvin Andrew Park, Billerica, MA (US); Desmond Allen Kaplan, Billerica, MA (US); Mark Ridgeway, Bremen (DE); Gary L. Glish, Chapel Hill, NC (US)

(73) Assignees: Bruker Daltonics, Inc., Billerica, MA (US); The University of North Carolina at Chapel Hill, Chapel Hill, NC (US)

( * ) Notice: Subject to any disclaimer, the term of this patent is extended or adjusted under 35 U.S.C. 154(b) by 111 days.

(21) Appl. No.: 13/115,424

(22) Filed: May 25, 2011

(65) Prior Publication Data

US 2012/0298860 A1 Nov. 29, 2012

(51) Int. Cl.
*H01J 3/14* (2006.01)
*B01D 59/44* (2006.01)

(52) U.S. Cl. ......... 250/290; 250/281; 250/288; 250/292

(58) Field of Classification Search ................ 250/294, 250/290, 281, 288, 287, 283, 432 R
See application file for complete search history.

(56) References Cited

U.S. PATENT DOCUMENTS

| | | | |
|---|---|---|---|
| 4,542,293 A | 9/1985 | Fenn | |
| 5,420,424 A | 5/1995 | Carnahan | |
| 5,811,800 A * | 9/1998 | Franzen et al. | 250/288 |
| 5,844,237 A | 12/1998 | Whitehouse | |
| 5,905,258 A | 5/1999 | Clemmer | |
| 5,965,884 A | 10/1999 | Laiko | |
| 6,455,846 B1 | 9/2002 | Prior et al. | |
| 6,504,149 B2 | 1/2003 | Guevremont | |
| 6,703,611 B2 | 3/2004 | Glish et al. | |
| 6,777,672 B1 * | 8/2004 | Park | 250/288 |
| 6,972,407 B2 | 12/2005 | Miller | |
| 7,339,166 B2 | 3/2008 | Tang | |
| 7,598,488 B2 * | 10/2009 | Park | 250/290 |
| 2002/0185606 A1 * | 12/2002 | Smith et al. | 250/423 R |
| 2003/0168591 A1 * | 9/2003 | Smith et al. | 250/288 |
| 2004/0089803 A1 * | 5/2004 | Foley | 250/288 |
| 2008/0042055 A1 * | 2/2008 | Baykut et al. | 250/287 |
| 2008/0067367 A1 * | 3/2008 | Park | 250/294 |
| 2008/0173809 A1 * | 7/2008 | Wu | 250/283 |
| 2011/0260048 A1 * | 10/2011 | Wouters et al. | 250/282 |

OTHER PUBLICATIONS

Schwartz, J., Senko, M. and Syka, J., "A Two-Dimensional Quadrupole Ion Trap Mass Spectrometer", Journal of the American Society for Mass Spectrometry, v. 13, pp. 659-669 (2002).

Hager, J. W., "A New Linear Ion Trap Mass Spectrometer", Rapid Communications in Mass Spectrometry, v. 16, pp. 512-526 (2002).

(Continued)

*Primary Examiner* — Jack Berman
*Assistant Examiner* — Johnnie L Smith
(74) *Attorney, Agent, or Firm* — O'Shea Getz P.C.

(57) ABSTRACT

Analyte ions are analyzed first by field asymmetric ion mobility spectrometry (FAIMS) before being analyzed by a mass analyzer. Analyte ions are produced at near atmospheric pressure and transferred via a dielectric capillary into the vacuum system of the mass analyzer. While passing through the capillary, the ions are analyzed by FAIMS via electrodes on the interior wall of the capillary. Improved ion transmission is achieved by providing smooth geometric transitions between the channel in FAIMS analyzer and the channel in the remainder of the capillary.

36 Claims, 4 Drawing Sheets

OTHER PUBLICATIONS

Kingdon, K. H., "A Method for the Neutralization of Electron Space Charge by Positive Ionization at Very Low Gas Pressures", Physical Review, v. 21, pp. 408-418 (1923).

Hu, Q., Noll, R. J., Li, H., Makarov, A., Hardman, M. and Cooks, R.G. "The Orbitrap: A New Mass Spectrometer", Journal of Mass Spectrometry, v. 40, pp. 430-443 (2005).

Torgerson, D.F., Skowronski, R.P. and MacFarlane, R.D., "New Approach to the Mass Spectroscopy of Non-volatile Compounds", Biochemical and Biophysical Research Communications, v. 60, n. 2, pp. 616-621 (1974).

Vanbreeman, R.B., Snow, M. and Cotter, R.J., "Time Resolved Laser Desorption Mass Spectrometry.—I Desorption of Preformed Ions", International Journal of Mass Spectrometry and Ion Physics, v. 49, pp. 35-50 (1983), Elsevier Scientific Publishing Company, Amsterdam, Netherlands.

Tabet, J.C. and Cotter, R.J., "Laser Desorption Time-of-Flight Mass Spectrometry of High Mass Molecules", Analytical Chemistry, v. 56, pp. 1662-1667 (1984).

Olthoff, J.K., Lys, I., Demirev, P. and Cotter, R.J., "Modification of Wiley-McLaren TOF Analyzers for Laser Desorption", Analytical Instrumentation, v. 16, n. 1, pp. 93-115 (1987).

Tanaka, K., Waki, H., Ido, Y., Akita, S., Yoshida, Y. and Yoshica, T., "Protein and Polymer Analyses up to m/z 100 000 by Laser Ionization Time-of-flight Mass Spectrometry", Rapid Communications in Mass Spectrometry, v. 2, n. 8, pp. 151-153 (1988).

Karas, M. and Hillenkamp, F., "Laser Desorption Ionization of Proteins with Molecular Masses Exceeding 10 000 Daltons", Analytical Chemistry, v. 60, pp. 2299-2301 (1988).

Dole, M., Mack, L.L., Hines, R.L., Mobley, R.C., Ferguson, L.D. and Alice, M.B., "Molecular Beams of Macroions", The Journal of Chemical Physics, v. 49, n. 5, pp. 2240-2249 (1968).

Chernushevich, I.V., Ens, W. and Standing, K.C., "Orthogonal Injection TOFMS for Analyzing Biomolecules", Analyical Chemistry News and Features, v. 71, n. 13, pp. 452A-461A (1999).

Takats, Z., Wiseman, J. M., Gologan, B. and Cooks, R.G., "Mass Spectrometry Sampling Under Ambient Conditions with Desorption Electrospray Ionization", Science, v. 306, pp. 471-473 (2004).

Buryakov, et al., "A New Method of Separation of Multi-Atomic Ions by Mobility at Atmospheric Pressure Using a High-Frequency Amplitude-Asymmetric Strong Electric Field", Int'l J of Mass Spectrom and Ion Processes, 128 (1993) 143-148, Elsevier Science Publishers B.V.

Reigner, et al., "Qualitative Evaluation of Field Ion Spectrometry for Chemical Warfare Agent Detection", 45th ASMS Conference on Mass Spectrometry and Allied Topics, Jun. 1-5, 1997, Palm Springs, CA US.

Srebalus, et al., "Gas-Phase Separations of Electrosprayed Peptide Libraries", Anal. Chem. 1999, 71, 3918-3927.

Taraszka, et al., "Mapping the Proteome of Drosophila Melanogaster: Analysi of Embryos and Adult Heads by LC-IMS-MS Methods", J Proteome Research 2005, 4, 1223-1237.

Wong, et al., "Evaluation of Ion Mobility Spectroscopy for Determining Charge-Solvated Versus Salt-Bridge Structures of Protonated Trimers", J. Am Soc Mass Spectrom 2005, 16, 1009-1019, Elsevier Inc.

Shvartsburg, et al., "Optimization of the Design and Operation of FAIMS Analyzers", J Am Soc Mass Spectrom 2005, 16, 2-12, Elsevier Inc.

Barnett, et al., "Application of ESI-FAIMS-MS to the Analysis of Tryptic Peptides", J Am Soc Mass Spectrom 2002, 13, 1282-1291, Elsevier Science Inc.

Ells, et al., "Detection of Chlorinated and Brominated Byproducts of Drinking Water Disinfection Using Electrospray Ionization—High-Field Asymmetric Waveform Ion Mobility Spectrometry-Mass Spectrometry", Anal. Chem., 1999, vol. 71, No. 20, pp. 4747-4752, American Chemical Society.

* cited by examiner

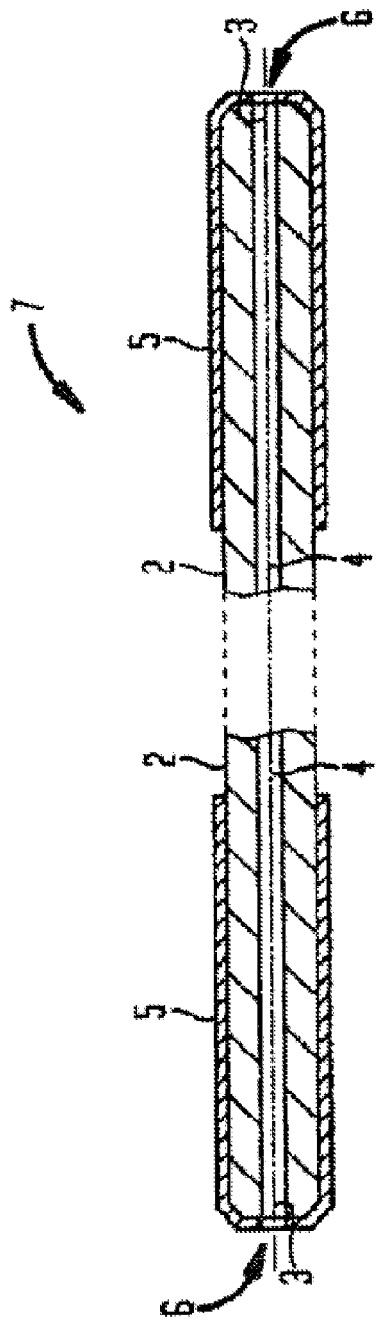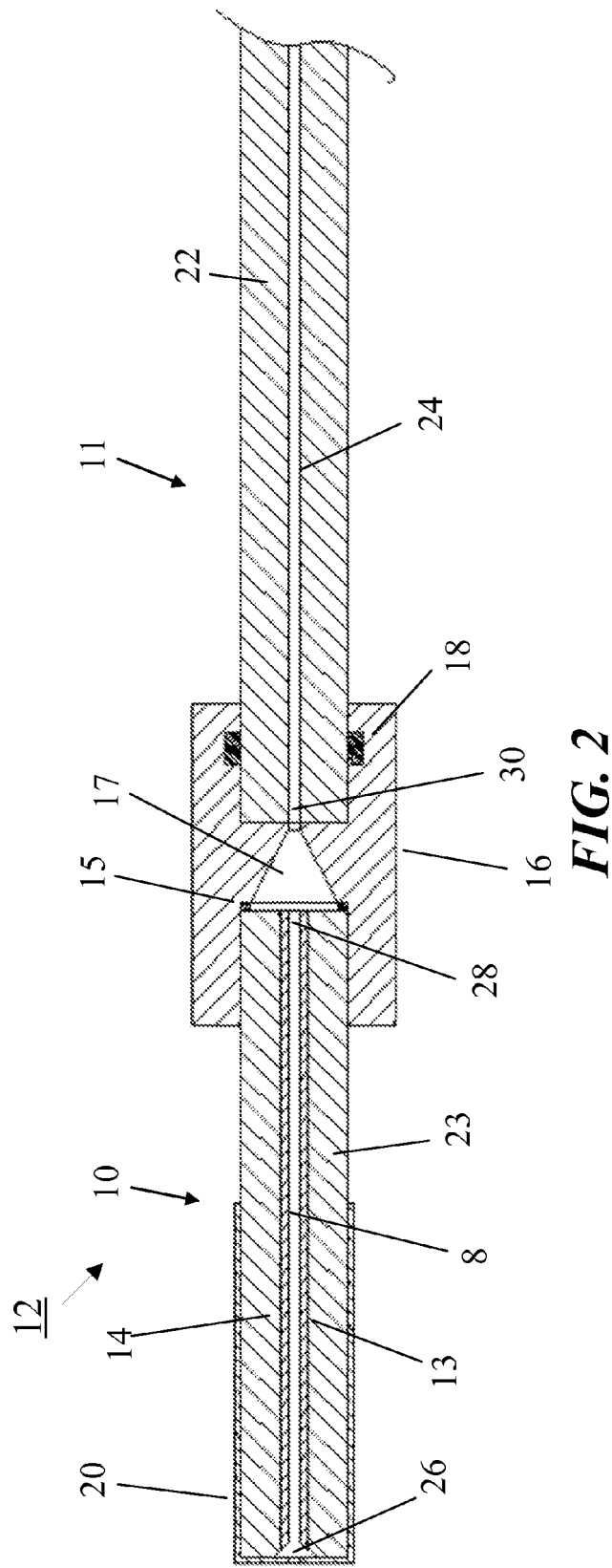

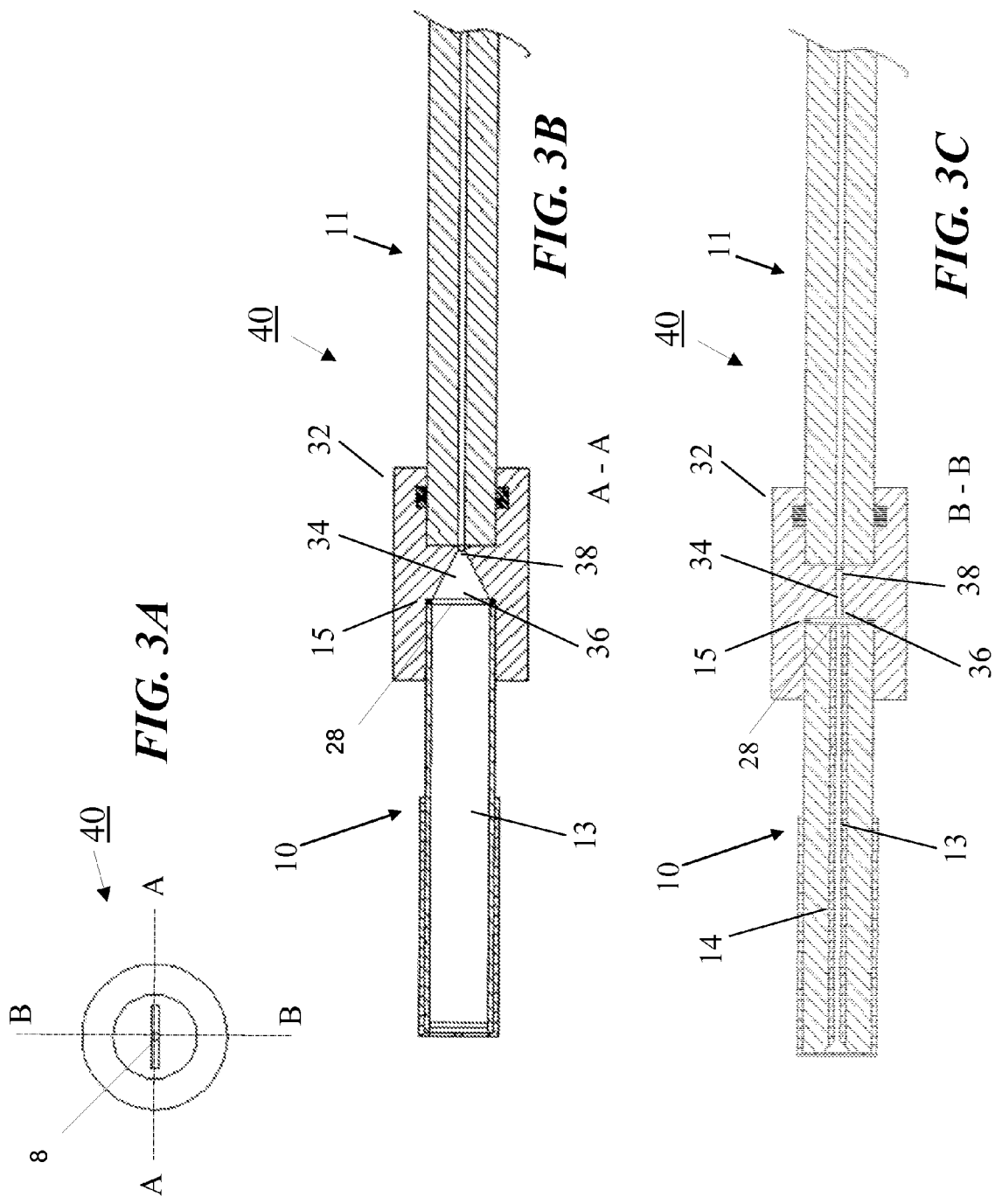

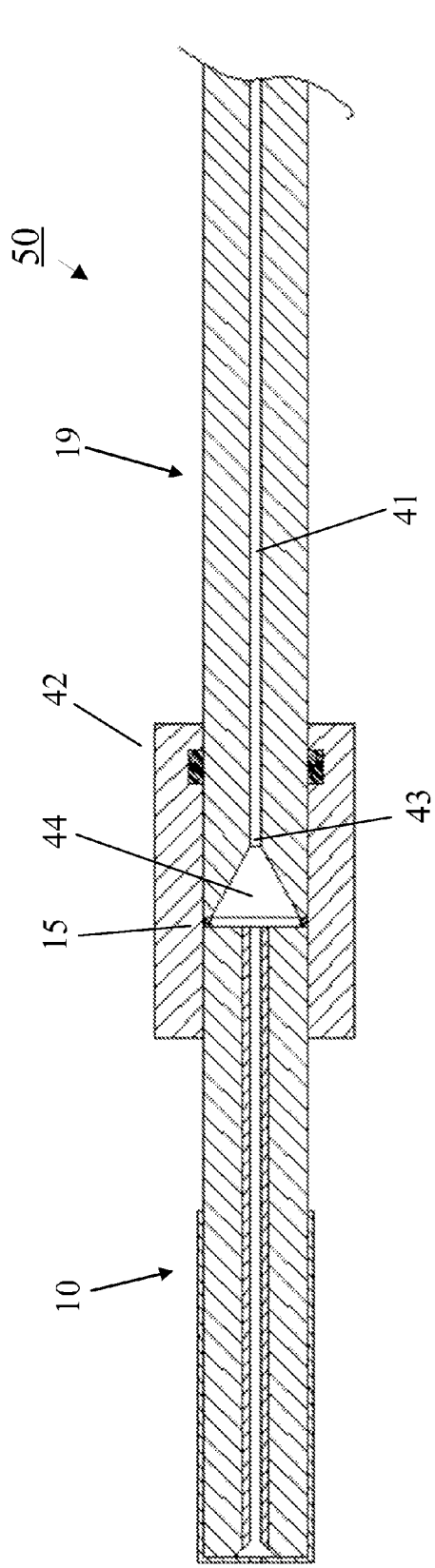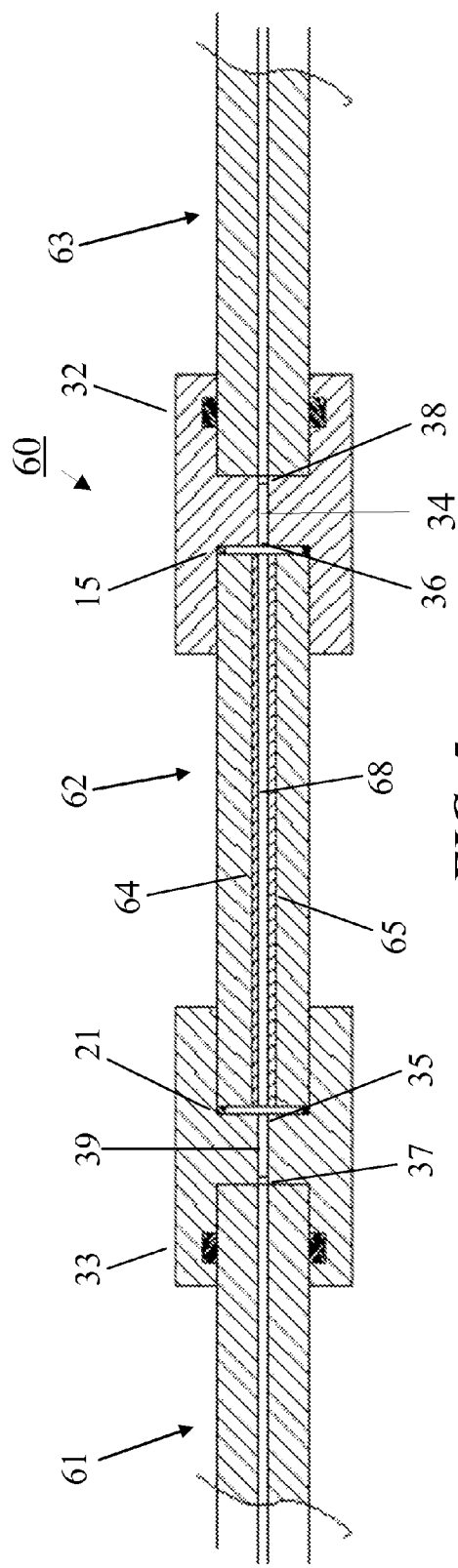

MEANS AND METHOD FOR FIELD ASYMMETRIC ION MOBILITY SPECTROMETRY COMBINED WITH MASS SPECTROMETRY

BACKGROUND

The present invention generally relates to an improved method and apparatus for the analysis of gas phase ions by field asymmetric ion mobility spectrometry and by mass spectrometry. The apparatus and methods for sample handling and analysis described herein are enhancements of the techniques referred to in the literature relating to mass spectrometry—an important tool in the analysis of a wide range of chemical compounds. Specifically, mass spectrometers can be used to determine the molecular weight of sample compounds. The analysis of samples by mass spectrometry consists of three main steps—formation of gas phase ions from sample material, mass analysis of the ions to separate the ions from one another according to ion mass, and detection of the ions. A variety of means and methods exist in the field of mass spectrometry to perform each of these three functions. The particular combination of the means and methods used in a given mass spectrometer determine the characteristics of that instrument.

To mass analyze ions, for example, one might use magnetic (B) or electrostatic (E) analysis, wherein ions passing through a magnetic or electrostatic field will follow a curved path. In a magnetic field, the curvature of the path will be indicative of the momentum-to-charge ratio of the ion. In an electrostatic field, the curvature of the path will be indicative of the kinetic energy-to-charge ratio of the ion. If magnetic and electrostatic analyzers are used consecutively, then both the momentum-to-charge and kinetic energy-to-charge ratios of the ions will be known and the mass of the ion will thereby be determined. Other well known mass analyzers are the quadrupole (Q), the ion cyclotron resonance (ICR), the time-of-flight (TOF), and the Paul ion trap analyzers. More recently, linear quadrupole ion traps [J. Schwartz, M. Senko, and J. Syka, *J. Am. Soc. Mass Spectrom.* 13, 659(2002); J. Hager, *Rapid Commun. Mass Spectrom.* 16, 512(2002)] have become more wide spread. And a new analyzer, the orbitrap, based on the Kingdon trap [K. Kingdon, *Phys. Rev.* 21, 408(1923)] was recently described by A. Makarov [Q. Hu et al., *J Mass Spectrom.* 40, 430(2005)]. Any form of mass analyzer may be used in conjunction with the means and method described here.

Before mass analysis can begin, gas phase ions must be formed from a sample material. If the sample material is sufficiently volatile, ions may be formed by electron ionization (EI) or chemical ionization (CI) of the gas phase sample molecules. Alternatively, for solid samples (e.g., semiconductors, or biological materials), ions can be formed by desorption and ionization of sample molecules by bombardment with high energy particles. Further, Secondary Ion Mass Spectrometry (SIMS), for example, uses keV ions to desorb and ionize sample material. In the SIMS process a large amount of energy is deposited in the analyte molecules, resulting in the fragmentation of fragile molecules. This fragmentation is undesirable in that information regarding the original composition of the sample (e.g., the molecular weight of sample molecules) will be lost.

For more labile, fragile molecules, other ionization methods now exist. The plasma desorption (PD) technique was introduced by Macfarlane et al. (R. D. Macfarlane, R. P. Skowronski, D. F. Torgerson, *Biochem. Biophys. Res Commoun.* 60 (1974) 616)("McFarlane"). Macfarlane discovered that the impact of high energy (MeV) ions on a surface, like SIMS would cause desorption and ionization of small analyte molecules. However, unlike SIMS, the PD process also results in the desorption of larger, more labile species (e.g., insulin and other protein molecules).

Additionally, lasers have been used in a similar manner to induce desorption of biological or other labile molecules. See, for example, Cotter et al. (R. B. VanBreeman, M. Snow, R. J. Cotter, *Int. J. Mass Spectrom. Ion Phys.* 49 (1983) 35; Tabet, J. C.; Cotter, R. J., Tabet, J. C., *Anal. Chem.* 56 (1984) 1662; or R. J. Cotter, P. Demirev, I. Lys, J. K. Olthoff, J. K.; Lys, I.: Demirev, P.: Cotter et al., R. J., *Anal. Instrument.* 16 (1987) 93). Cotter modified a CVC 2000 time-of-flight mass spectrometer for infrared laser desorption of non-volatile biomolecules, using a Tachisto (Needham, Mass.) model 215G pulsed carbon dioxide laser. The plasma or laser desorption and ionization of labile molecules relies on the deposition of little or no energy in the analyte molecules of interest.

The use of lasers to desorb and ionize labile molecules intact was enhanced by the introduction of matrix assisted laser desorption ionization (MALDI) (K. Tanaka, H. Waki, Y. Ido, S. Akita, Y. Yoshida, T. Yoshica, *Rapid Commun. Mass Spectrom.* 2 (1988) 151 and M. Karas, F. Hillenkamp, *Anal. Chem.* 60 (1988) 2299). In the MALDI process, an analyte is dissolved in a solid, organic matrix. Laser light of a wavelength that is absorbed by the solid matrix but not by the analyte is used to excite the sample. Thus, the matrix is excited directly by the laser, and the excited matrix sublimes into the gas phase carrying with it the analyte molecules. The analyte molecules are then ionized by proton, electron, or cation transfer from the matrix molecules to the analyte molecules. This process (i.e., MALDI) is typically used in conjunction with time-of-flight mass spectrometry (TOFMS) and can be used to measure the molecular weights of proteins in excess of 100,000 Daltons.

Atmospheric Pressure Ionization (API) includes a number of ion production means and methods. Among these are atmospheric pressure chemical ionization (APCI), atmospheric pressure photoionization (APPI), electrospray ionization (ESI), and desorption electrospray ionization (ESI). Typically, analyte ions are produced from liquid solution at atmospheric pressure. ESI, one of the more widely used methods, was first suggested for use with mass spectrometry by Dole et al. (M. Dole, L. L. Mack, R. L. Hines, R. C. Mobley, L. D. Ferguson, M. B. Alice, *J. Chem. Phys.* 49, 2240, 1968). In the electrospray technique, analyte is dissolved in a liquid solution and sprayed from a needle. The spray is induced by the application of a potential difference between the needle and a counter electrode. The spray results in the formation of fine, charged droplets of solution containing analyte molecules. In the gas phase, the solvent evaporates leaving behind charged, gas phase, analyte ions. This method allows for very large ions to be formed. Ions as large as 1 MDa have been detected by ESI in conjunction with mass spectrometry (ESMS).

In addition to ESI, many other ion production methods might be used at atmospheric or elevated pressure. For example, MALDI has recently been adapted by Laiko et al. to work at atmospheric pressure (Victor Laiko and Alma Burlingame, "Atmospheric Pressure Matrix Assisted Laser Desorption", U.S. Pat. No. 5,965,884, and Atmospheric Pressure Matrix Assisted Laser Desorption Ionization, poster #1121, 4th International Symposium on Mass Spectrometry in the Health and Life Sciences, San Francisco, Aug. 25-29, 1998) and by Standing et al. at elevated pressures (Time of Flight Mass Spectrometry of Biomolecules with Orthogonal Injection+Collisional Cooling, poster #1272, 4th International Symposium on Mass Spectrometry in the Health and Life Sciences, San Francisco, Aug. 25-29, 1998; and Orthogonal Injection TOFMS *Anal. Chem.* 71(13), 452A (1999)). The benefit of adapting ion sources in this manner is that the ion optics (i.e., the electrode structure and operation) in the mass analyzer and mass spectral results obtained are largely independent of the ion production method used.

The elevated pressure MALDI source disclosed by Standing differs from what is disclosed by Laiko et al. Specifically, Laiko et al. disclose a source intended to operate at substantially atmospheric pressure. In contrast, the source disclosed by Standing et al. is intended to operate at a pressure of about 70 mtorr.

More recently, Takats et al. [Z. Takats, J. M. Wiseman, B. Gologan, and R. G. Cooks, Science 306, 471(2004)] introduced yet another atmospheric pressure ionization method known as desorption electrospray ionization (DESI). According to Takats et al., DESI is a method for producing ions from analyte on a surface. Electrosprayed charged droplets and ion of solvent are directed at the surface under study. The impact of the charged droplets on the surface results in the desorption and ionization of the analyte to form gas phase analyte ions.

Gas phase ions may be analyzed via any of the above described mass analyzers, via an ion mobility analyzer, or by a combination of mass and mobility analyzers. Ion mobility spectrometry (IMS) is a method whereby the "mobility" of analyte ions through a gas is measured under the influence of a static electric field. IMS is described in detail in the literature [see, for example, G. Eiceman and Z. Karpas, Ion Mobility Spectrometry (CRC. Boca Raton, Fla. 1994); and Plasma Chromatography, edited by T. W. Carr (Plenum, New York, 1984)]. At low electric field strengths—e.g. a few kilovolts per meter—the speed of analyte ions through a gas is measured. To start the measurement, ions are pulsed into the entrance of the mobility analyzer. Ions of a given mobility travel the length of the drift tube of the mobility analyzer at fixed velocity resulting from the balance in force between the electric field pushing ions forward and drag on the ions due to collisions with the gas. At the far end of the analyzer, the ions strike a detector and are detected. By measuring the time between the introduction of ions into the analyzer and the detection of the ions, the speed of the ions, and therefore their mobility can be determined.

At low field strengths, the mobility of an ion is a constant relating the speed of the ion to the strength of the electric field. However, at high electric field strengths, the mobility of the ions varies with electric field strength. This gives rise to field asymmetric ion mobility spectrometry (FAIMS)—an extension of IMS which takes advantage of the change in ion mobility at high field strengths.

FAIMS is based on an observation of Mason and McDaniel [W. McDaniel and Edward A. Mason, The mobility and diffusion of ions in gases, John Wiley & Sons, 1973] who found that the mobility of an ion varies with the applied electric field strength. Above an electric field to gas density ratio (E/N) of 40 Td (E>10,700 V/cm at atmospheric pressure) the mobility coefficient K(E) has a non-linear dependence on the field. This dependence is believed to be specific for each ion species. A coefficient "a" describes the change in mobility as a function of field strength and is defined as the fractional change in mobility when comparing a high field strength condition to a low field strength condition. An $\alpha$ value of 0.1, for example, represents an increase of 10% in the ion's mobility whereas an $\alpha$ value of −0.1 represents a decrease of 10% in the ion's mobility.

FAIMS is described in detail in the literature [I. Buryakov, E. Krylov, E. Nazarov, and U. Rasulev, Int. J. Mass Spectrom. Ion Phys. 128. 143 (1993); D. Riegner, C. Harden, B. Carnahan, and S. Day, Proceedings of the 45th ASMS Conference on Mass Spectrometry and Allied Topics, Palm Springs, Calif., Jun. 1-4, 1997, p. 473; B. Carnahan, S. Day, V. Kouznetsov, M. Matyjaszczyk, and A. Tarassov, Proceedings of the 41st ISA Analysis Division Symposium, Framingham, Mass., Apr. 21-24, 1996, p. 85; and B. Carnahan and A. Tarassov, U.S. Pat. No. 5,420,424]. FAIMS devices measure the difference in the mobility of an ion at high field relative to its mobility at low field. That is, the ions are separated on the basis of the compound dependent behavior of mobility as a function of electric field strength. In the prior art FAIMS devices such as described in U.S. Pat. No. 6,972,407, herein incorporated by reference, two parallel, planar conducting electrodes are used to generate an electric field in which analyte ions are to be analyzed. The analyte ions are entrained in a carrier gas which moves at high velocity (several meters per second) perpendicular to the electric field—i.e. parallel to the surface of the planar conducting electrodes. Applying the appropriate potentials to the "top" and "bottom" electrodes will result in the filtering of ions on the basis of their $\alpha$ value. As described in the prior art literature, a rectangular waveform having repeatedly a high potential and then a low potential is applied between the electrodes. For a relatively short period of time, a high potential is applied between the electrodes and then for a longer period of time a relatively low potential of opposite polarity is applied. The magnitude of the potentials and the duration of their application are such that the time averaged potential difference is zero. During the application of the high potential ions will drift laterally with a mobility $K(1+\alpha)$. During the application of the low potential of opposing polarity, the ions will drift laterally with a mobility K and in the opposite direction to that when the high potential was applied. Applying an additional DC "compensation voltage" between the electrodes allows the selection of ions of a given mobility difference to be transmitted.

In recent years, IMS and FAIMS spectrometers have been combined with mass spectrometry. In U.S. Pat. No. 5,905,258 Clemmer and Reilly combine IMS with a time of flight mass spectrometer (TOFMS). This provided for a first analysis of the ions by IMS followed by a second analysis via TOFMS. Ultimately, this yields a two dimensional plot containing both the mobility and mass of the ions under investigation. The advantages of this type of combined analyzer over a mass spectrometer alone are described in detail in the literature [C. S. Srebalus et al., *Anal. Chem.* 71(18), 3918(1999); J. A. Taraszka et al., *J. Proteom. Res.* 4, 1223(2005); R. L. Wong, E. R. Williams, A. E. Counterman, and D. Clemmer, *J. Am. Soc. Mass Spectrom.* 16, 1009(2005)] and include the separation of chemical background from analyte species for an improved signal-to-noise ratio (S/N), and the separation of ions based on compound class or charge state for easier mass spectral interpretation.

Similarly, in U.S. Pat. No. 6,504,149, for example, Guevremont et al. combine a FAIMS device with a mass spectrometer. As detailed in the literature, a combined FAIMS mass spectrometer has similar advantages as an IMS mass spectrometer [A. Shvartsburg, K. Tang, R. Smith, *J. Am. Soc. Mass Spectrom.* 16, 2(2005); D. A. Barnett, B. Ells, R. Guevremont, and R. W. Purves, *J. Am. Soc. Mass Spectrom.* 13, 1282 (2002)]. For example, a combined FAIMS mass spectrometer has an improved signal-to-noise ratio over a mass spectrometer alone because the FAIMS device can filter away the chemical background.

In the instrument disclosed by Guevremont, the FAIMS device is imposed between the ion production means and the inlet to the mass spectrometer. That is, a FAIMS device may be added to a preexisting mass spectrometer by moving the ion production means and placing the FAIMS apparatus between the inlet to the mass spectrometer and the ion production means. As a result, the transmission efficiency of analyte ions from the ion production means to the mass analyzer is reduced. Although the S/N in the mass spectra produced may be improved over a mass spectrometer alone, the imposition of the FAIMS device nonetheless leads to a reduced sensitivity.

Furthermore prior art FAIMS devices have been employed as peripheral or add-on devices when used in conjunction with mass spectrometers [B. Ells et al, *Anal. Chem.* 71, 4747 (1999)]. That is, prior art FAIMS devices are not highly integrated with mass spectrometers and users or technicians must mount and demount the FAIMS device in order to run tandem FAIMS/MS or MS—only experiments, respectively. That is, if a prior art FAIMS apparatus is implemented on a mass spectrometer then it must be kept in operation in order to be of any benefit. In order to observe the entire range of ions being generated by the ion production means—i.e. without filtering via FAIMS—the asymmetric waveform must be turned off. However, the presence of the FAIMS device between the ion source and the mass spectrometer—even if deactivated—would represent a loss of ion transmission efficiency and therefore a loss in sensitivity. Thus, in a practical operation, the FAIMS apparatus must be implemented between the ion production means and the inlet of the mass spectrometer when FAIMS filtering is desired and the FAIMS apparatus must be removed again when FAIMS filtering is not desired. This added complexity discourages users from adopting FAIMS in combination with mass spectrometry.

If gas phase ions produced via an API method are to be analyzed in a mass spectrometer, they must first be transported from the ionization region through regions of differing pressures and ultimately to a mass analyzer for subsequent analysis (e.g., via time-of-flight mass spectrometry (TOFMS), Fourier transform mass spectrometry (FTMS), etc.). In some prior art sources, this was accomplished through use of a small orifice between the ionization region and the vacuum region. In conventional instruments, the orifice is circular, however, in U.S. Pat. No. 7,339,166, Tang et al. recognize that the ion transmission efficiency between FAIMS analyzers of planar geometry and mass analyzers at reduced pressures can be improved by changing the shape of the orifice or by using a multitude of orifices. Specifically, a " . . . conductance limit aperture having the geometry of a rectangle . . . provides a more efficient coupling of planar . . . FAIMS to downstream stages . . . . "

In other prior art, metal or dielectric capillaries have been used to transmit ions entrained in a carrier gas from a high pressure ion production region into the vacuum chamber of mass spectrometers—see, for example, Fenn et al., U.S. Pat. No. 4,542,293 and Whitehouse et al., U.S. Pat. No. 5,844,237. In U.S. Pat. No. 6,777,672, incorporated herein by reference, Park describes a multiple section capillary for interfacing various ion production means and for transporting ions into the vacuum chamber of a mass spectrometer.

An example of a prior art transfer capillary is shown in FIG. 1. As depicted, capillary 7 comprises a generally cylindrical glass tube 2 having an internal bore 4. The ends of capillary 7 include a metal coating (e.g., platinum, copper, etc.) to form conductors 5 which encompass the outer surface of capillary 7 at its ends, leaving a central aperture 6 such that the entrance and exit to internal bore 4 are left uncovered. Conductors 5 may be connected to electrical contacts (not shown) in order to maintain a desired space potential at each end of capillary 7. In operation, a first electrode (one of conductors 5) of capillary 7 may be maintained at an extreme negative potential (e.g. −4,500V). This first electrode 5 acts as the entrance end of the capillary and resides at near atmospheric pressure. Positively charged analyte ions formed in the atmospheric pressure ion production region are attracted to the first electrode 5 and are entrained in the gas flow into the capillary. A second electrode (the other of conductors 5), acts as the exit end of the capillary and resides at the pressure of the first vacuum region of the mass spectrometer. This second of conductors 5 may form the first stage of a multi-stage lensing system for the final direction of the ions to the spectrometer, and may be maintained at a positive potential (e.g., 160 volts).

Importantly, ions are carried through the transfer capillary by entrainment in gas which is pumped from the ion production region, through the capillary, into the first vacuum region of the mass spectrometer. Typically, the gas pressure at the capillary inlet is about one atmosphere whereas the pressure at the capillary outlet, into the first pumping region, is between one and three millibar. Under these conditions, the velocity of the gas in the capillary is about 100 m/s. It is the "force" associated with this high velocity gas that is able to drive the ions away from the electrically attractive potential at the capillary entrance and towards the electrically repulsive potential at the capillary exit.

In other prior art, Glish et al. (U.S. Pat. No. 6,703,611) and Prior et al. (U.S. Pat. No. 6,455,846) independently describe transfer capillaries having flared entrances. According to Glish, the value of their flared capillary is that it "has increased positional alignment tolerances and . . . is capable of both single and multiple nanoelectrospray and standard electrospray ionization." According to Prior, their flared capillary "provides greater efficiency in the transmission of gaseous ions from an ion source situated in a region of relatively high pressure, to the interior of a device maintained at a relatively low pressure."

Finally, in U.S. Pat. No. 7,598,488, incorporated herein by reference, Park describes the integration of a FAIMS analyzer into an ion transfer capillary. In one embodiment, the transfer capillary is a multisection capillary having the FAIMS analyzer integrated in a first section of the capillary and having a union by which the first capillary section can be removably joined with a second section of the capillary. According to Park, "the transmission efficiency of analyte ions [through a FAIMS analyzer integrated into the ion transfer capillary] is improved over prior art FAIMS devices"

However, the prior art does not describe any means or mechanism that provides a smooth transition between a FAIMS analyzer in a first section of capillary and a second section of the capillary. For example, a FAIMS analyzer in a first capillary section having a first geometric cross section—for example, rectangular—joined with a second section of capillary having a second cross section—for example, round—will result in a geometric discontinuity at the union between the two sections. Such a discontinuity leads, in prior art devices to turbulent gas flow, dead volumes, and a reduction in the transmission of ions from the outlet of the FAIMS analyzer into the downstream vacuum system and analyzers. Similarly, in a contiguous capillary, the cross section of the capillary in that part of the capillary which includes the FAIMS analyzer may differ from the remainder of the capillary. The geometric discontinuity between the FAIMS analyzer and the remainder of the capillary results in a loss of ion transmission.

SUMMARY

It is therefore one purpose of the present invention to provide a means and method for a tandem FAIMS/MS instrument wherein the FAIMS device is integrated into or removably joined with the ion transfer capillary of the mass spectrometer such that the transmission efficiency of analyte ions is improved over prior art FAIMS devices and such that the FAIMS device need not be demounted when not in use.

In one embodiment, a contiguous or multisection transfer capillary having a FAIMS analyzer integrated in one of the sections thereof has an improved geometric transition between the FAIMS analyzer and the remainder of the capillary such that the transmission of ions from an ion production region to a first vacuum region via said capillary is improved over prior art FAIMS/MS devices.

In another embodiment, the FAIMS analyzer is integrated in a first section of a multi-section transfer capillary. The cross sectional geometry of the FAIMS analyzer may be any shape, such as rectangular. The first section is removably joined with a second section of capillary via a union piece. The second section of capillary has a channel through it which is cylindrically symmetric and small in comparison to the cross section of the FAIMS analyzer.

In alternate embodiments, the bore through the second section of capillary may be cylindrically asymmetric and may have any cross sectional geometry. The union piece has a channel through it by which the channels of the first and second capillary sections are joined and includes a means of forming a substantially gas tight seal between the first and second capillary sections. The channel of the union piece is cylindrically symmetric and funnel shaped such that it can receive gas and ions over a wide cross sectional area from the first capillary section and efficiently focus them down and into the second capillary section.

In alternate embodiments, the geometric transition—i.e. in the channel of the union—may be from any first cross sectional geometry which best accepts gas and ions from the first capillary section and the FAIMS analyzer therein to any second cross sectional geometry which best transmits gas and ions into the second capillary section. For example, the FAIMS analyzer in the first capillary section may have a planar geometry and therefore a rectangular cross section whereas the bore of the second capillary section is cylindrical. The inlet of the union would therefore be rectangular, and its outlet would be round, and the channel of the union would have a smooth transition between the rectangular entrance and circular exit.

In further alternate embodiments, the second section of capillary may have a multitude of bores therethrough. In such a case the geometric transition in the channel of the union piece may be from an inlet of geometry best suited to accept gas and ions from the first capillary section to a multitude of outlets each of which is aligned with a bore in the second capillary section.

In still other alternate embodiments, the channel in the union piece may be eliminated such that the first capillary section directly abuts the second capillary section or is offset from the second capillary section by an insulating spacer. The funnel shaped geometric transition is incorporated into the entrance end of the second capillary section in the form of a flare at the entrance of the second section's bore.

In yet other alternate embodiments, the capillary is contiguous having a channel and a FAIMS analyzer integrally incorporated therein. The cross section in the channel of the portion of the capillary containing the FAIMS analyzer may differ from that in the rest of the capillary. Such embodiments incorporate smooth geometric transitions between the channel of the portion of the capillary containing the FAIMS analyzer and the channel in the rest of the capillary.

In alternate embodiments, the capillary is contiguous and the FAIMS analyzer is integrated at a selected position along the length of the capillary, but neither at the entrance or exit end of the capillary. The cross section in the portion of the capillary containing the FAIMS analyzer may differ from that in the rest of the capillary. Such embodiments incorporate smooth geometric transitions both into and out of the channel of the portion of the capillary containing the FAIMS analyzer.

Similarly, a FAIMS analyzer may be integrated in the middle section of a three section capillary. In such an embodiment, unions between sections provide smooth geometric transitions into as well as out of the FAIMS analyzer.

BRIEF DESCRIPTION OF THE DRAWINGS

A further understanding of the present invention can be obtained by reference to an embodiment set forth in the illustrations of the accompanying drawings. Although the illustrated embodiment is merely exemplary of systems for carrying out the present invention, both the organization and method of operation of the invention, in general, together with further objectives and advantages thereof, may be more easily understood by reference to the drawings and the following description. The drawings are not intended to limit the scope of this invention, which is set forth with particularity in the claims as appended or as subsequently amended, but merely to clarify and exemplify the invention.

For a more complete understanding of the present invention, reference is now made to the following drawings in which:

FIG. 1 shows a partial cut-away cross sectional view of a prior art capillary comprising a unitary dielectric tube having a cylindrical outer surface and internal bore;

FIG. 2 depicts a multiple section capillary with incorporated FAIMS electrodes and a union according to the present invention;

FIG. 3A depicts an end view of a multiple section capillary with FAIMS electrodes incorporated in a first section and a union piece having a rectangular opening at its entrance end, a circular opening at its exit end, and a smooth transition between the two;

FIG. 3B depicts a cross sectional view taken at line A-A in FIG. 3A of a multiple section capillary with FAIMS electrodes incorporated in a first section and a union piece having a rectangular opening at its entrance end, a circular opening at its exit end, and a smooth transition between the two;

FIG. 3C depicts a cross sectional view taken at line B-B in FIG. 3A of a multiple section capillary with FAIMS electrodes incorporated in a first section and a union piece having a rectangular opening at its entrance end, a circular opening at its exit end, and a smooth transition between the two;

FIG. 4 depicts a multiple section capillary with FAIMS electrodes incorporated in a first capillary section, a union, and a second capillary section having a bore with a flared entrance end;

FIG. 5 depicts a three section capillary having FAIMS electrodes incorporated in a middle capillary section.

DETAILED DESCRIPTION

Figure 6:
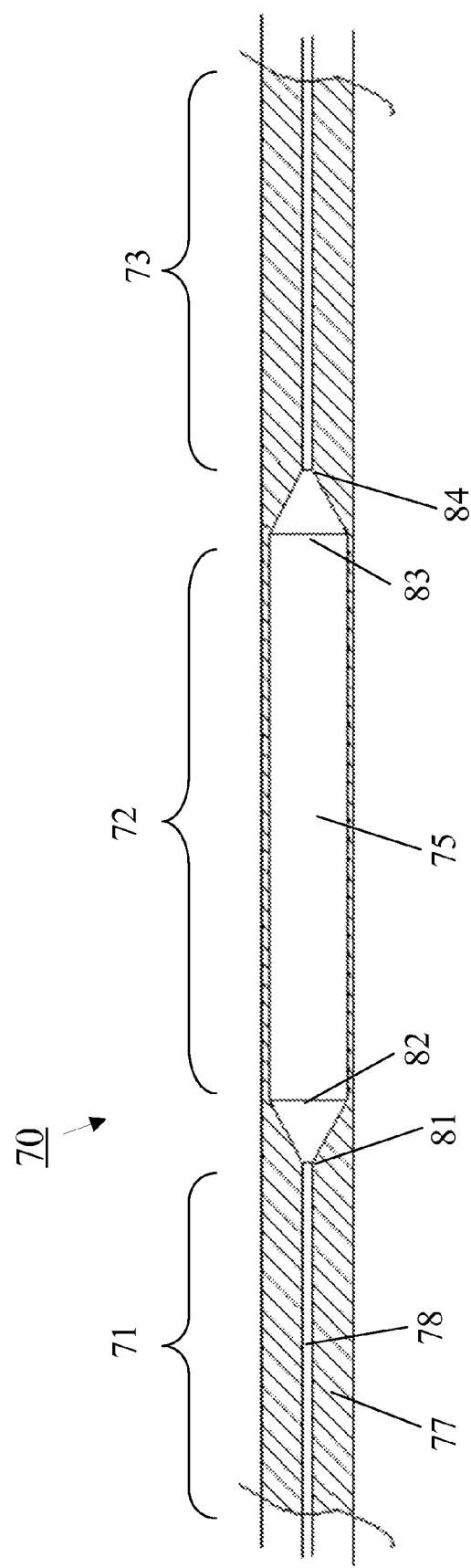
FIG. 6 depicts a contiguous capillary with incorporated FAIMS electrodes and smooth geometric transitions into and out of the volume between the FAIMS electrodes.

As required, a detailed illustrative embodiment of the present invention is disclosed herein. However, techniques, systems and operating structures in accordance with the present invention may be embodied in a wide variety of sizes, shapes, forms and modes, some of which may be quite different from those in the disclosed embodiment. Consequently, the specific structural and functional details disclosed herein are merely representative, yet in that regard, they are deemed to afford the best embodiment for purposes of disclosure and to provide a basis for the claims herein which define the scope of the present invention.

The following presents a detailed description of one embodiment of the present invention, as well as some alternate embodiments of the invention. As discussed above, the present invention relates generally to the mass spectroscopic analysis of chemical samples and more particularly to mass spectrometry. Specifically, a means and method is described for the tandem FAIMS/MS analysis of a sample.

Reference is herein made to the figures, wherein the numerals representing particular parts are consistently used throughout the figures and accompanying discussion.

Referring first to FIG. 2, shown is an embodiment according to the present invention wherein multiple section capillary 12 consists of two capillary sections 10 and 11. While the construction may vary widely, in this specific embodiment, section 11 has dimensions and general construction similar to prior art capillary 7. Section 11 has a body 22 constructed primarily of a dielectric—i.e. glass, ceramic, etc. —and a central bore 24 through which gas and ions may pass. The outer surface and inner bore of section 11 are both substantially cylindrical. In operation, section 11 is fixed in the source of a mass spectrometer in a manner similar to that described in the prior art. That is, entrance end 30 of section 11 is fixed in an ion production region at near atmospheric pressure whereas the exit end of section 11 (not shown) is fixed in the first pumping region of the mass spectrometer. Capillary section 11 might have a wide variety of diameters and lengths, however, as an example, the inner and outer diameters of section 11 might be 0.7 and 6.5 mm respectively and the length of section 11 might be 180 mm.

Capillary section 10 also has a body 23 formed from dielectric material. Channel 8 of section 10 is bounded on two sides by planar FAIMS electrodes 13 and 14. A wide variety of dimensions may be chosen for channel 8 and electrodes 13 and 14, however, as an example, the gap between electrodes 13 and 14 may be 0.7 mm. Electrodes 13 and 14 may be any desired width, however, as an example may be 5.5 mm wide—i.e. perpendicular to the page. Thus, channel 8 may, for example, be rectangular in cross section having dimension of 0.7 mm by 5.5 mm. FAIMS electrodes 13 and 14 may be any length, however, here are chosen to be 38.6 mm long. Also, FAIMS electrodes 13 and 14 may be composed of any electrically conducting material and may be of any desired thickness. However, as an example, FAIMS electrodes 13 and 14 are 0.2 mm thick.

Capillary section 10 may have any desired length and diameter, however, as an example, section 10 may have a length of 40 mm and an outer diameter of 6.5 mm. Entrance end 26 of section 10 includes a conductive sheath 20. Sheath 20 may be composed of any electrically conducting material—e.g. Pt, Ni, etc. Exit end 28 of section 10 may be fixed in union 16 by, for example, epoxy. Electrically insulating spacer 15 having the shape of a ring 0.5 mm thick is used to electrically isolate electrodes 13 and 14 from union 16. In alternate embodiments spacer 15 may have any dimensions or may be left out. Union 16 is composed of electrically conducting material and has channel 17 through it by which channels 8 and 24 of capillary sections 10 and 11 respectively are joined. Channel 17 of union 16 is cylindrically symmetric and funnel shaped such that it can receive gas and ions over a wide cross sectional area from the first capillary section 10 and efficiently focus them down and into second capillary section 11. Union 16 includes o-ring 18 such that union 16 together with section 10 may be removably joined with capillary section 11. As discussed above, when FAIMS filtering of analyte ions is desired, section 10 together with union 16 are joined with section 11. In operation, a FAIMS waveform is applied between electrodes 13 and 14 as described above. When FAIMS analysis is not desired, section 10 and union 16 may be left away and only section 11 is used to transmit ions into the mass spectrometer's vacuum system.

In alternate embodiments, the geometric transition—i.e. in the channel of a union—may be from any first cross sectional geometry which best accepts gas and ions from a first capillary section and a FAIMS analyzer therein to any second cross sectional geometry which best transmits gas and ions into a second capillary section. FIG. 3A depicts an end view of multiple section capillary 40. FIGS. 3B and 3C depict cross sectional views of multiple section capillary 40 taken at lines A-A and B-B respectively. In the embodiment depicted in FIGS. 3A-3C, first capillary section 10 includes channel 8 which has a rectangular cross section whereas the bore of second capillary section 11 is cylindrical. Union piece 32, used to join sections 10 and 11, has all the features and characteristics of union piece 16 except that channel 34 is not cylindrically symmetric. Rather, inlet 36 of channel 34 is rectangular, and outlet 38 is circular. Furthermore, channel 34 has a smooth geometric transition between rectangular entrance 36 and circular exit 38. Inlet 36 and outlet 38 may have any of a wide variety of dimensions, however, as an example, inlet 36 is 5.5 by 0.7 mm and outlet 38 is 0.7 mm in diameter. Notice that rectangular inlet 36 of union 32 is aligned with rectangular shaped outlet 28 of section 10.

In further alternate embodiments, capillary section 11 may have a multitude of circular bores therethrough. In such embodiments, the geometric transition in channel 34 of union piece 32 may be from inlet 36 having rectangular cross section, or alternatively any other geometry suited to accept gas and ions from first capillary section 10, to a multitude of circular outlets each of which is aligned with a bore in second capillary section 11. The dimensions of the inlets and outlets of alternative union pieces are similar, though not necessarily identical, to the dimensions of the orifices in the outlets and inlets of upstream and downstream respectively, capillary sections.

In further alternate embodiments, the channel in the union piece may be eliminated such that the first capillary section directly abuts the second capillary section or is offset from the second capillary section by an insulating spacer. The funnel shaped geometric transition is incorporated into the entrance end of the second capillary section in the form of a flare at the entrance of the second section's bore. As an example, multi-bore capillary 50 depicted in cross section in FIG. 4 includes capillary sections 10 and 19 and union 42. Union piece 42, used to join sections 10 and 19, has all the features and characteristics of union piece 16 except that it includes no channel through which gas and ions would flow. Rather, capillary sections 10 and 19 are separated only by insulating spacer 15. Capillary section 19 includes all the features and characteristics of capillary section 11; however, bore 41 of section 19 also includes funnel shaped flare 44 at entrance end 43. In this way, the geometric transition between capillary sections 10 and 19 lies not in union 42, but in the body of section 19. In alternate embodiments, any other geometric transition having any desired dimensions may be incorporated into the body of capillary section 19.

Referring next to FIG. 5, shown is an embodiment according to the present invention wherein multiple section capillary 60 consists of three capillary sections 61, 62 and 63. Capillary sections 61 and 63 are constructed in a manner similar to capillary section 11, however, sections 61 and 63 may be shorter—for example 90 mm long—than capillary section 11. According to this embodiment, when incorporated in a mass spectrometer, the inlet of capillary section 61 resides in the ion source region whereas the outlet of capillary section 63 resides in the first pumping region of the mass spectrometer.

Capillary section 62 is constructed in substantially the same manner as capillary section 10 with the exception that the equivalent of electrically conducting sheath 20 is missing from section 62. Channel 68 of section 62 is bounded on two sides by planar FAIMS electrodes 64 and 65. The gap between electrodes 64 and 65 is 0.7 mm and electrodes 64 and 65 are 5.5 mm wide—i.e. perpendicular to the page—and 38.6 mm long. Thus, channel 68 is rectangular in cross section having dimension of 0.7 mm by 5.5 mm.

Insulating spacer 21 is identical to spacer 15. Also, union 33 is identical to union 32 but is rotated 180°. Thus, end 37 of channel 39 is circular whereas end 35 is rectangular. Capillary sections 61 and 63 are removably joined with capillary section 62 via unions 33 and 32 respectively. When fully assembled into capillary 60, gas and ions from the upstream ion production region pass through capillary section 62 and enter end 37 of channel 39. As it passes through channel 39, the channel expands to fill the rectangular cross section of end 35 before passing into section 62. The gas and ions pass through capillary section 62 and into rectangular opening 36 in union 32. In channel 34, the gas and ions are focused down to circular opening 38 before passing out into section 63 and on to the downstream mass analyzer. Thus, capillary 60 provides a smooth geometric transition both into and out of the FAIMS analyzer of capillary section 62 via unions 33 and 32 respectively.

In alternate embodiment 70, depicted in cross section in FIG. 6, a similar construction is provided, but in a unitary capillary design. Capillary 70 has a body 77 comprised of dielectric material with channel 78 through it. In alternate embodiments, the outer surface of capillary 70 may have any desired dimensions, however, in the current embodiment, body 77 has an outer diameter of 6.5 mm along its entire length. Capillary 70 is 180 mm long with an entrance end (to the left, off the page) and an exit end (to the right, off the page). Gas and ions enter channel 78 through the entrance end of the capillary, located in an ion production region of a mass spectrometer. The gas and ions pass through channel 78 to the exit end located in the first vacuum region of the mass spectrometer. In region 71, channel 78 is cylindrically symmetric, having a diameter of 0.7 mm. Moving from left to right, at point 81, channel 78 begins to transition to a rectangular cross section. At point 82 and in the entire region 72, channel 78 has a rectangular cross section of dimensions 5.5 mm wide and 0.7 mm high. In region 72, channel 78 is bounded on two sides by FAIMS electrodes only one of which—electrode 75—is shown. The opposite FAIMS electrode is positioned parallel to and 0.7 mm from electrode 75—i.e. above the page. Both FAIMS electrodes are 5.5 mm wide and 38.6 mm long. At point 83 channel 78 begins to transition back to a circular channel. At point 84 and in the entire region 73, channel 78 again is cylindrically symmetric, having a diameter of 0.7 mm. As discussed above, ions carried through channel 78 in a stream of gas may be analyzed for their differential mobility by applying an appropriate asymmetric RF waveform between the FAIMS electrodes in region 72. Alternatively, if a neutral potential is applied to the FAIMS electrodes—e.g. ground—then ions will pass unaffected through capillary 70 to the downstream mass analyzer.

It should be noted that while the present invention is described in conjunction with FAIMS, means for other methods—for example, for production, fragmentation, or reaction of ions, or for the optical spectroscopy of analyte in the capillary—might be incorporated in the above described capillaries in addition to or instead of FAIMS.

Furthermore, it should be understood that a FAIMS analyzer incorporated in a capillary according to the present invention need not be used in conjunction with a mass spectrometer. In alternate embodiments, the FAIMS analyzer as incorporated in a capillary according to the present invention may be itself be incorporated into instrument having an ion source at an elevated pressure and an ion detector and/or other analytical device in a vacuum chamber. As discussed above, ions would be transmitted between the elevated pressure ion source and the vacuum chamber via the channel in the capillary and FAIMS analyzer. In one such alternate embodiment, only a detector—for example a Faraday cup, a phonon detector, or a CCD—is used to detect the ions. In such an embodiment, one may use the FAIMS analyzer in conjunction with the detector to generate a FAIMS spectrum of ions produced in the ion source. In another alternate embodiment any known gas phase means of manipulating the ions might be employed in the vacuum chamber. Such means for manipulating the ions may include, for example, irradiation with light of selected wavelengths followed by fluorescence detection. In yet further alternate embodiments, the vacuum system may contain a means of capturing the FAIMS selected ions intact. Such means may, for example, comprise a solid surface or liquid medium onto/into which the selected ions are "soft landed". After collecting the selected ions, one may perform any further solid, liquid, or gas phase analytical tests known from the prior art.

While the present invention has been described with reference to one or more preferred and alternate embodiments, such embodiments are merely exemplary and are not intended to be limiting or represent an exhaustive enumeration of all aspects of the invention. The scope of the invention, therefore, shall be defined solely by the following claims. Further, it will be apparent to those of skill in the art that numerous changes may be made in such details without departing from the spirit and the principles of the invention. It should be appreciated that the present invention is capable of being embodied in other forms without departing from its essential characteristics.

What is claimed is:

1. Apparatus for combining field asymmetric ion mobility spectrometry (FAIMS) with an analytical device having an ion source region with a first pressure and a vacuum region having a second pressure less than the first pressure, comprising:
  a transfer capillary with a bore having a geometric bore inlet cross-section and which transfers gas and ions from the ion source region towards the vacuum region;
  a FAIMS analyzer located between the ion source region and the transfer capillary and having a geometric outlet cross section that differs from the bore inlet cross section; and
  a geometric transition region, which is located between the FAIMS analyzer and the transfer capillary and has a shape that provides a smooth transition between the FAIMS analyzer outlet cross section and the bore inlet cross section such that transmission of ions from the ion source region to the vacuum region is maximized.

2. The apparatus of claim 1 wherein the transfer capillary is a multi-section capillary comprising a plurality of physically separate sections and the FAIMS analyzer is constructed in a first section of the multi-section transfer capillary.

3. The apparatus of claim 2 wherein the first section of the multi-section transfer capillary is removably joined with a second section of the multi-section transfer capillary via a union piece.

4. The apparatus of claim 3 wherein geometric transition region is in the union piece.

5. The apparatus of claim 3 wherein the first section and the second section of the multi-section capillary are separated by an insulating spacer.

6. The apparatus of claim 3 wherein the union piece has a channel therethrough by which the outlet of the FAIMS analyzer is connected to the inlet of the second section and comprises means of forming a substantially gas tight seal between the FAIMS analyzer and the second section.

7. The apparatus of claim 6 wherein the channel of the union piece is cylindrically symmetric and funnel shaped.

8. The apparatus of claim 6, wherein a second section of the multi-section transfer capillary has a multitude of bores therethrough and the channel of the union piece connects the outlet of the FAIMS analyzer to a multitude of outlets each of which is aligned with a bore in the second section of the multi-section transfer capillary.

9. The apparatus of claim 2 wherein a second section of the multi-section transfer capillary has cylindrically symmetric bore therethrough with an inlet cross section that is smaller that the outlet cross section of the FAIMS analyzer.

10. The apparatus of claim 1 wherein the geometric outlet cross section of the FAIMS analyzer is rectangular.

11. The apparatus of claim 1 wherein the geometric transition region is part of the transfer capillary bore in the form of a flare at the transfer capillary bore inlet.

12. The apparatus of claim 1 wherein the transfer capillary comprises three physically separate sections and the FAIMS analyzer is constructed in a middle section of the multi-section transfer capillary.

13. The apparatus of claim 12 further comprising a second geometric transition region, which is located between the first section of the multi-section transfer capillary and the FAIMS analyzer and has a shape that provides a smooth transition between the bore inlet cross section of the first section and a FAIMS analyzer inlet cross section such that transmission of ions from the ion production region to the vacuum region is maximized.

14. The apparatus of claim 1 wherein the analytical device comprises one of a mass spectrometer, an ion detector, a device for irradiating FAIMS selected ions with light of selected wavelengths and detecting fluorescence of the FAIMS selected ions and a device for capturing FAIMS selected ions intact.

15. Apparatus for combining field asymmetric ion mobility spectrometry (FAIMS) with an analytical device having an ion source region with a first pressure and a vacuum region having a second pressure less than the first pressure, comprising:
   a transfer capillary with a bore having a cross section and which transfers gas and ions from the ion source region towards the vacuum region;
   a FAIMS analyzer located within the transfer capillary bore, the FAIMS analyzer having a geometric cross section that differs from the transfer capillary bore cross section; and
   a geometric transition region, which is located between the FAIMS analyzer and the transfer capillary bore and has a shape that provides a smooth transition between the FAIMS analyzer cross section and the bore cross section such that transmission of ions from the ion production region to the vacuum region is maximized.

16. The apparatus of claim 15 wherein the FAIMS analyzer is located at a position along the length of the transfer capillary, which position is not at an entrance or an exit of the transfer capillary.

17. The apparatus of claim 16 wherein the geometric transition region connects an outlet of the FAIMS analyzer to the transfer capillary bore and a second geometric transition region connects the transfer capillary bore to an inlet of the FAIMS analyzer.

18. The apparatus of claim 15 wherein the analytical device comprises one of a mass spectrometer, an ion detector, a device for irradiating FAIMS selected ions with light of selected wavelengths and detecting fluorescence of the FAIMS selected ions and a device for capturing FAIMS selected ions intact.

19. A method for combining field asymmetric ion mobility spectrometry (FAIMS) with an analytical device having an ion source region with a first pressure and a vacuum region having a second pressure less than the first pressure, comprising:
   (a) providing a transfer capillary with a bore having a geometric bore inlet cross-section to transfer gas and ions from the ion source region towards the vacuum region;
   (b) positioning a FAIMS analyzer between the ion source region and the transfer capillary, the FAIMS analyzer having a geometric outlet cross section that differs from the bore inlet cross section; and
   (c) positioning a geometric transition region between the FAIMS analyzer and the transfer capillary, the geometric transition region having a shape that provides a smooth transition between the FAIMS analyzer outlet cross section and the bore inlet cross section such that transmission of ions from the ion source region to the vacuum region is maximized.

20. The method of claim 19 wherein the transfer capillary is a multi-section capillary comprising a plurality of physically separate sections and step (b) comprises constructing the FAIMS analyzer in a first section of the multi-section transfer capillary.

21. The method of claim 20 wherein step (a) comprises removably joining the first section of the multi-section transfer capillary with a second section of the multi-section transfer capillary via a union piece.

22. The method of claim 21 wherein step (c) comprises positioning the geometric transition region in the union piece.

23. The method of claim 21 further comprising separating the first section and the second section of the multi-section capillary by an insulating spacer.

24. The method of claim 21 wherein the union piece has a channel therethrough by which the outlet of the FAIMS analyzer is connected to the inlet of the second section and the method further comprises forming a substantially gas tight seal between the FAIMS analyzer and the second section.

25. The method of claim 24 wherein the channel of the union piece is cylindrically symmetric and funnel shaped.

26. The method of claim 24, wherein a second section of the multi-section transfer capillary has a multitude of bores therethrough and step (c) comprises connecting the outlet of the FAIMS analyzer to a multitude of outlets, each of which is aligned with a bore in the second section of the multi-section transfer capillary, with the channel of the union piece.

27. The method of claim 20 wherein step (a) comprises providing a second section of the multi-section transfer capillary with a cylindrically symmetric bore therethrough and an inlet cross section that is smaller that the outlet cross section of the FAIMS analyzer.

28. The method of claim 19 wherein the geometric outlet cross section of the FAIMS analyzer is rectangular.

29. The method of claim 19 wherein step (c) comprises providing the geometric transition region as part of the transfer capillary bore in the form of a flare at the transfer capillary bore inlet.

30. The method of claim 19 wherein step (a) comprises providing the transfer capillary in three physically separate sections and step (b) comprises constructing the FAIMS analyzer in a middle section of the multi-section transfer capillary.

31. The method of claim 30 further comprising locating a second geometric transition region between the first section of the multi-section transfer capillary and the FAIMS analyzer, the second geometric transition region having a shape that provides a smooth transition between the bore inlet cross section of the first section and a FAIMS analyzer inlet cross section such that transmission of ions from the ion production region to the vacuum region is maximized.

32. The method of claim 19 wherein the analytical device comprises one of a mass spectrometer, an ion detector, a device for irradiating FAIMS selected ions with light of selected wavelengths and detecting fluorescence of the FAIMS selected ions and a device for capturing FAIMS selected ions intact.

33. A method for combining field asymmetric ion mobility spectrometry (FAIMS) with an analytical device having an ion source region with a first pressure and a vacuum region having a second pressure less than the first pressure, comprising:

(a) providing a transfer capillary with a bore having a cross section to transfer gas and ions from the ion source region towards the vacuum region;

(b) constructing a FAIMS analyzer within the transfer capillary bore, the FAIMS analyzer having a geometric cross section that differs from the transfer capillary bore cross section; and (c) locating a geometric transition region between the FAIMS analyzer and the transfer capillary bore, the geometric transition region having a shape that provides a smooth transition between the FAIMS analyzer cross section and the bore cross section such that transmission of ions from the ion production region to the vacuum region is maximized.

34. The method of claim 33 wherein step (b) comprises constructing the FAIMS analyzer at a position along the length of the transfer capillary, which position is not at an entrance or an exit of the transfer capillary.

35. The method of claim 34 wherein step (c) comprises locating the geometric transition region to connect an outlet of the FAIMS analyzer to the transfer capillary bore and the method further comprises locating a second geometric transition region to connect the transfer capillary bore to an inlet of the FAIMS analyzer.

36. The method of claim 33 wherein the analytical device comprises one of a mass spectrometer, an ion detector, a device for irradiating FAIMS selected ions with light of selected wavelengths and detecting fluorescence of the FAIMS selected ions and a device for capturing FAIMS selected ions intact.

* * * * *